United States Patent [19]

Lepper et al.

[11] Patent Number: 4,520,211

[45] Date of Patent: May 28, 1985

[54] PROCESS FOR THE CONTINUOUS PREPARATION OF POLYHYDRIC ALCOHOLS

[75] Inventors: Herbert Lepper, Köln-Mühlheim; Hartwig Schütt, Düsseldorf-Benrath, both of Fed. Rep. of Germany

[73] Assignee: Henkel Kommanditgesellschaft auf Aktien, Düsseldorf-Holthausen, Fed. Rep. of Germany

[21] Appl. No.: 583,145

[22] Filed: Feb. 24, 1984

Related U.S. Application Data

[63] Continuation of Ser. No. 386,598, Jun. 9, 1982, abandoned.

[30] Foreign Application Priority Data

Nov. 7, 1981 [DE] Fed. Rep. of Germany ....... 3144320

[51] Int. Cl.³ .................. C07C 31/26; C07C 29/14
[52] U.S. Cl. ..................................... 568/863; 502/325
[58] Field of Search ......................................... 568/863

[56] References Cited

U.S. PATENT DOCUMENTS

| 2,868,847 | 1/1959 | Boyers | 568/863 |
| 3,173,959 | 3/1965 | Rittmeister | 568/885 |
| 3,963,788 | 6/1976 | Kruse et al. | 568/863 |
| 3,963,789 | 6/1976 | Kruse et al. | 568/863 |
| 4,292,206 | 9/1981 | Barnes et al. | 252/477 R |
| 4,366,093 | 12/1982 | Shiozaki et al. | 252/477 R |

Primary Examiner—J. E. Evans
Attorney, Agent, or Firm—Hammond & Littell, Weissenberger & Dippert

[57] ABSTRACT

This invention is directed to the preparation of polyhydric alcohols. More specifically, this invention is directed to a continuous process for preparing polyhydric alcohols by the hydrogenation of carbohydrates in the presence of ruthenium-containing catalysts at elevated temperatures and elevated pressure, the improvement wherein the catalyst comprises a catalyst solid bed of ruthenium carrier catalyst in lumps.

11 Claims, 1 Drawing Figure

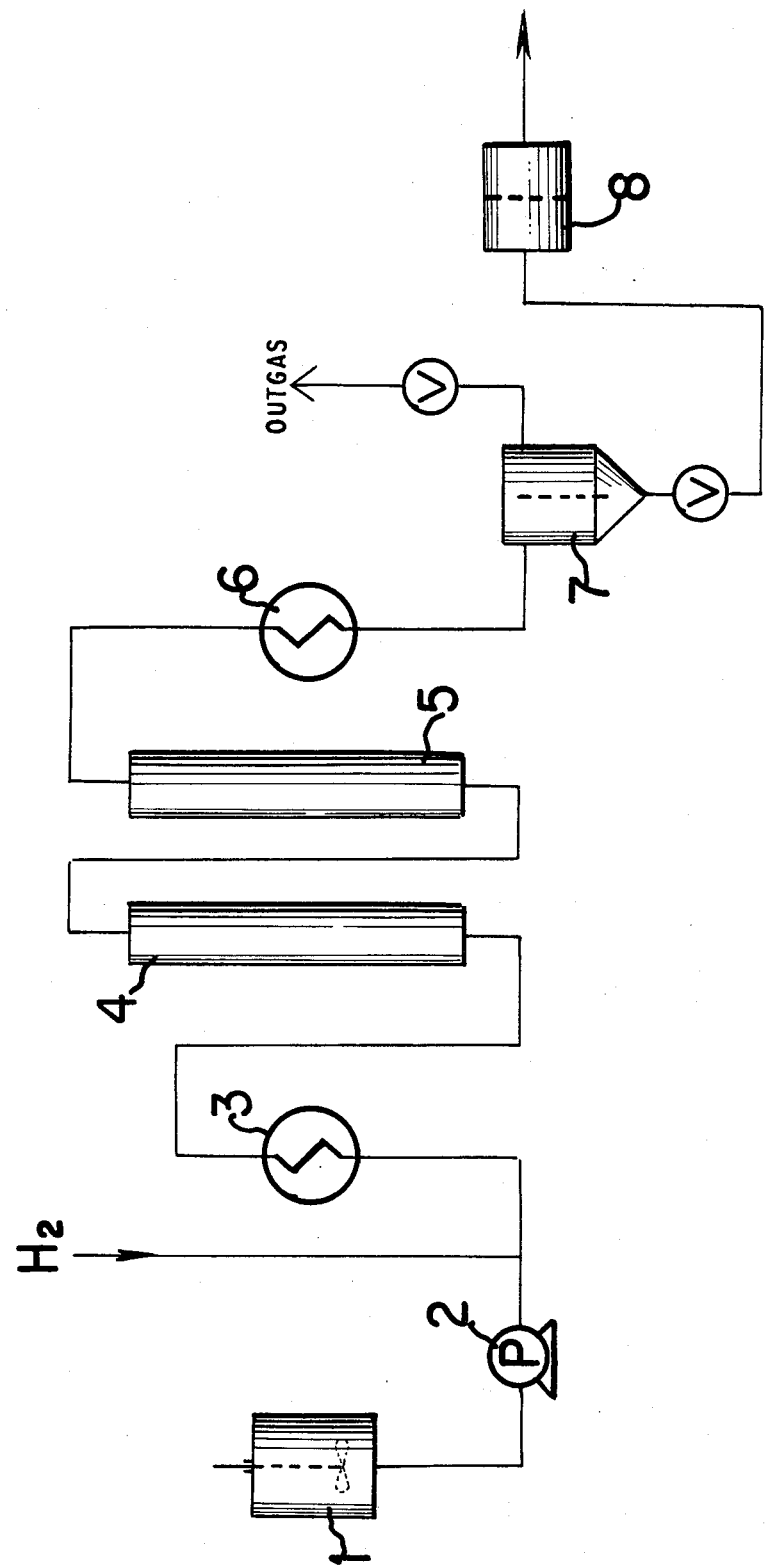

PROCESS FOR THE CONTINUOUS PREPARATION OF POLYHYDRIC ALCOHOLS

This is a continuation Ser. No. 386,598 filed June 9, 1982 now abandoned.

FIELD OF THE INVENTION

This invention is directed to the preparation of polyhydric alcohols. More specifically, this invention is directed to an improved process for the preparation of polyhydric alcohols by catalytic hydrogenation of carbohydrates in the presence of ruthenium carrier catalysts.

BACKGROUND OF THE INVENTION

The conversion of carbohydrates into polyhydric alcohols (sugar alcohols) under hydrogenation conditions and in the presence of ruthenium on solid carrier materials is known. For example, U.S. Pat. No. 2,868,847, describes a process for the catalytic hydrogenation of carbohydrates in which ruthenium on inert carrier materials such as carbon, aluminum oxide, silicon dioxide, kieselguhr, silica gel, or diatomaceous earth, is used as catalyst. The carbohydrates used include monosaccharides such as dextrose and fructose and disaccharides such as sucrose and lactose. Dextrose was hydrogenated to sorbitol, and sucrose and lactose were hydrolyzed and hydrogenated to hexitols.

Moreover, the use of ruthenium on animal charcoal as catalyst in the hydrogenation of monosaccharides is described by N. A. Vasyunina et al. in *Izv. Akad. Nauk. SSR Khimicheskaya*, 4 (1969), p. 848–854. Methods for the catalytic hydrogenation of carbohydrates in the presence of ruthenium on crystalline aluminosilicate clay or of ruthenium-zeolite catalysts are known from German published application (DE-OS) No. 2,555,856 and the patent literature cited therein.

It has previously been proposed to continuously carry out the catalytic hydrogenation of carbohydrates in the presence of suspended finely divided ruthenium carrier catalysts (see, U.S. Pat. No. 2,868,847 and German published application (DE-OS) No. 2,555,856). However, this procedure is characterized by a number of serious disadvantages. First, employing the catalyst in suspension hydrogenation in finely divided form makes it necessary to remove the catalyst from the resulting reaction mixture by complicated filtration systems. Second, quantitative elimination of the catalyst is necessary, not only just to purify the hydrogenation products. When precious metal catalysts are used, as in the present case, their virtually quantitative recovery is also a prerequisite for the profitability of the process. Besides, it has been found that the ruthenium carrier catalysts separated after the hydrogenation show a reduced activity when re-used, so that the ruthenium carrier catalysts must be regenerated after the third pass at the latest. If the separated catalysts has to be regenerated or processed for recovery of ruthenium, it must be freed from the adhering hydrogenation product by intensive washing. Here, too, it is disadvantageous that the catalyst is present as a fine powder. Third, in continuous hydrogenation with suspended catalysts there is a danger that sedimentation will lead to clogging in the reactors and other parts of the hydrogenation installation. And lastly, the abrasiveness of the catalyst carrier material causes increased wear of the installation parts coming in contact with the suspension.

OBJECTS OF THE INVENTION

It is an object of the invention to provide an improved process for preparing polyhydric alcohols.

It is also an object of the invention to provide a process for preparing polyhydric alcohols by catalytic hydrogenation of carbohydrates in the presence of ruthenium carrier catalysts.

It is a further object of the invention to overcome the above-mentioned disadvantages of known procedures.

It is a yet further object of the invention to provide a continuous process for the preparation of polyhydric alcohols by the hydrogenation of carbohydrates in the presence of ruthenium-containing catalyst at elevated temperature and elevated pressure, wherein the catalyst comprises a catalyst solid bed of ruthenium carrier catalyst in lumps.

These and other objects of the invention will become more apparent in the discussion below.

BRIEF DESCRIPTION OF THE DRAWING

The drawing is a schematic representation of one procedure that may be employed to carry out catalytic hydrogenation of carbohydrates.

DETAILED DESCRIPTION OF THE INVENTION

Applicants have developed a process which overcomes the disadvantages mentioned above. According to Applicants' invention, polyhydric alcohols are prepared in a continuous procedure by the hydrogenation of carbohydrates in the presence of ruthenium-containing catalysts at elevated temperature and elevated pressure, wherein the catalyst comprises a catalyst solid bed of ruthenium carrier catalysts in lumps.

With regard to this disclosure, the term "carbohydrate" includes monosaccharides and polysaccharides, and these may be pure compounds such as glucose, fructose, and sucrose, as well as saccharide mixtures such as, for example, starch hydrolyzates. The term "polysaccharide" denotes saccharides with more than one monosaccharide unit, that is, di-, tri-, and oligosaccharides. Moreover, the term "conversion" as used herein refers to hydrogenation when applied to monosaccharides and to a combination of hydrogenation and hydrolysis when applied to polysaccharides.

The terminology "catalyst solid bed" refers to a stationary arrangement of the catalyst in the reactor in the manner of a packed bed. Conducting hydrogenation on solid-bed catalysts is known per se (see, for example, *Ullmanns Enzyklopadie der technischen Chemie*, 4th ed., Vol. 13, pp. 135 et.seq.

Catalysts useful according to the invention include all ruthenium-containing solid catalysts employed for the hydrogenation of carbohydrates to the corresponding polyhydric alcohols. This particularly involves catalysts in which the catalytically active metallic ruthenium is precipitated in finely divided form onto suitable carrier materials such as aluminum oxide, titanium dioxide, kieselguhr, silica gel, molecular sieves, and zeolites of natural or synthetic origin. Catalysts whose carrier material consists of active carbon are preferred. According to the invention, these carrier catalysts are employed as finely divided powders as before, but in compacted lumpy form.

The catalysts under consideration usually contain from about 0.1 to 10 percent by weight, preferably from about 1 to 4 percent by weight, of elemental ruthenium, based upon the total weight of the catalyst. If desired, catalysts with a higher content of active metal, such as up to about 30 percent by weight, may be used.

The ruthenium-containing carrier catalysts can be produced by methods known from the literature. For instance, the carrier material may be impregnated with a ruthenium salt solution, and then the impregnated material is dried in a stream of a reducing gas and heated to the decomposition temperature.

For use in the process of the invention the ruthenium-containing carrier catalysts are shaped into lumpy form, for example, spherical, cylindrical, or hollow-cylindrical form, by known techniques, such as tablet-forming, pelletizing, and extruding, optionally with addition of binding agents.

The particle size of the catalyst employed in lumpy form may vary widely. On the one hand, the catalyst particles should not be so small that the flow resistance of the catalysts solid bed greatly hinders the through-flow of the charged mixture of hydrogen and aqueous carbohydrate solution and necessitates too high a pressure. On the other hand, the maximum dimensions of the lumpy ruthenium carrier catalyst are given by the reactor geometry. As is known, the ratio of reactor diameter to the diameter of the catalyst particle or moiety should, for hydrodynamic reasons, not fall below a value of from about 7 to 10 (see, J. Falbe and U. Hasserodt, *Katalysatoren, Tenside and Mineraloladditive*, Stuttgart (1978), page 21). As a rule, the particle size of the catalyst lumps, i.e., the diameter and/or length of the catalyst particles, will be selected so that it is in the range of from about 2 to 10 mm.

Starting materials for the process of the invention include monosaccharides and a mixture thereof and materials containing polysaccharides. The expression "materials containing polysaccharides" encompasses disaccharides and mixtures thereof as well as carbohydrates which contain both monosaccharides and polysaccharides. Examples of suitable monosaccharides are fructose, galactose, mannose, arabinose, ribose, xylose, and, in particular, glucose. The pentoses and hexoses are the most important monosaccharides. The process of the invention is generally applicable to monosaccharides with at least 4 carbon atoms, more particularly to those with from 5 to 7 carbon atoms, and sugars with terminal aldehyde groups (aldoses) as well as those with a non-terminal keto group (ketoses) enter into consideration.

Examples of suitable disaccharides include lactose, maltose, sucrose, cellobiose, and melibiose. A suitable trisaccharide is raffinose.

Additional polysaccharide-containing starting materials include starch degradation products, for example, dextrin, glucose syrup, and starch hydrolyzates such as corn starch hydrolyzates, as well as cellulose hydrolyzates.

The above-mentioned starting materials are subjected to the process of the invention in the form of aqueous solutions of suitable concentration. Generally the hydrogenation is carried out with solutions in the concentration range of from about 20 to 80 percent by weight. Solutions with concentrations in the range of from about 40 to 70 percent by weight are preferred. It is not absolutely necessary that the carbohydrates to be hydrogenated form true solutions with the water; colloidal solutions or suspensions of carbohydrates can also be subjected to the process of the invention.

In the practice of the process of the invention, the aqueous solution of the carbohydrate to be hydrogenated together with hydrogen is passed continuously through a reaction zone containing the solid bed of ruthenium carrier catalyst in lumps. The temperature of the reaction zone may vary within wide limits. In general, reaction temperatures of from about 60° to 200° C. are applicable, the temperature range of from about 90° to 160° C. being preferred. Especially in the hydrogenation of glucose it is advisable not to exceed temperatures of 160° C., if possible, as glucose tends to caramelize above this temperature. It has proven desirable to heat the mixture of aqueous substrate solution and hydrogen to the intended reaction temperature prior to entrance into the reaction zone.

The reaction pressure is at least 25 bar and may assume values up to 500 bar. Reaction pressures in the range of from about 100 to 300 bar are preferred.

The pH value of the aqueous substrate solutions is generally near the neutral point, that is, about 7. This especially applies to the hydrogenation of monosaccharides. If in the hydrogenation of starting material containing polysaccharide a hydrolytic splitting of the glucoside bonds is to additionally be brought about, then the pH value of the substrate solution should be in the range of from about 2.5 to 4.5, preferably in the range of from about 3.0 to 4.0. Adjustment of the pH value can be effected with a mineral acid which in the required concentration does not attack the reactor material, for example, sulfuric acid or phosphoric acid. Naturally, only those ruthenium catalysts whose carrier material is acid-stable are suitable when the process of the invention is carried out in the acid pH range. It is obviously important to maintain the enumerated low pH values during the last reaction phase. For this reason, it may be advisable to supply the required acid in the middle or in the second half of the reaction zone.

The following examples are intended to illustrate the invention and should not be construed as limiting the invention thereto.

EXAMPLES

The testing described below was carried out in a test set-up corresponding to the Drawing. The components of the test set-up comprised storage vessel 1 with agitator, delivery pump 2, heater 3, two series-connected reactors 4 and 5, cooler 6, separator 7, and filtering equipment 8. The reactors 4 and 5 each have a capacity of 4.2 liters and each have an inside diameter of 70 mm.

The respective degrees of conversion were each determined by determining the residual content of reducing sugars in the hydrogenation product. For this purpose, samples of the reaction product were diluted with water, heated with Fehling's solution, and mixed with potassium iodide. Thereafter the iodine released by cuprous iodide was titrated with sodium thiosulfate solution, starch solution being used as indicator.

COMPARISON EXAMPLE

The hydrogenation of glucose described hereafter was carried out in the apparatus shown in the Drawing. A commercial ruthenium carrier catalysts (2 percent by weight of Ku on active carbon) was used as catalysts.

A 50 percent by weight glucose solution (d=1.22 gm/ml) in which 0.4 percent by weight, based upon the weight of the glucose, of catalyst was suspended, was conveyed out of storage vessel 1 by means of pump 2 in a continuous stream together with hydrogen into the heater 3, where the charged mixture was brought to a temperature of 150° C. Thereafter, at 150° C. and under a pressure of 250 bar, the mixture of glucose solution, catalyst, and hydrogen passed through the reaction zone consisting of two-series connected reactors 4 and 5, each having a capacity of 4.2 liters (diameter 70 mm). Then the reaction mixture passed through cooler 6 in which it was cooled to 30° to 40° C. and passed on to the separator 7 where the excess hydrogen was separated. After expansion of the hydrogenation product to atmospheric pressure, the catalyst was separated in after-connected filtering equipment 8.

At a throughput of 4 liters of glucose solution per hour and an hourly H$_2$ expansion of 12 Nm$^3$, a 99% conversion of the glucose was obtained.

The filtered catalyst was used a second and a third time. In the second pass a slightly reduced activity of the catalyst was observed; under the same conditions as in the first pass a 95% conversion of the glucose was obtained. In the third pass the catalyst showed a drastic decrease in activity; a glucose conversion of only 25% was obtained.

Hence, under the conditions of suspension hydrogenation, the ruthenium catalyst employed can as a practical matter be re-used only once without regeneration.

If the mean catalyst activity ($\bar{a}_k$) is defined as the quantity of hydrogenation product sorbitol formed per quantity unit of catalyst in both passes, and if a mean conversion of 97% is taken as basis for both passes, a value of $$\bar{a}_k = \frac{2 \times 0.97 \times 100 \times m.\ \text{wt. (sorbitol)}}{0.4 \times m.\ \text{wt. (glucose)}} = 490$$

(m.wt.=molecular weight) is obtained for the suspension process. Conversely, for the catalyst requirement, a value of 0.204 percent by weight, based upon the total quantity of sorbitol obtained from glucose in both passes, is calculated. When the precious metal content of the carrier catalyst is taken into account, a ruthenium requirement of $4.1 \times 10^{-3}$ percent by weight is obtained.

EXAMPLE 1

For the hydrogenations according to the invention described below, the apparatus according to the Drawing was modified so that a mixture of sugar solution and hydrogen, having passed through the heater 3, was passed through the series-connected reactors 4 and 5 from above. Also, the filtering equipment 8 was removed.

A commercial compacted ruthenium carrier catalyst (2 percent by weight of Ru on animal charcoal, cylindrical form, diameter 2 mm, length 2 to 5 mm) was used as catalyst. The two reactors 4 and 5 were filled with a total of 3.12 kg of catalyst in lumps.

A 50 percent by weight glucose solution (d=1.22 gm/ml) was conveyed from storage vessel 1 via pump 2 in a continuous stream together with hydrogen into heater 3, where the mixture was heated to 150° C. Then, at 150° C. and 250 bar, the mixture passed through the reactors 4 and 5 filled with lump catalyst. Thereafter the reactor mixture was cooled to 30° to 40° C. in cooler 6 and was finally separated from excess hydrogen in separator 7.

The throughput of the glucose solution was selected so that the glucose content of the hydrogenation product did not exceed 0.5 percent by weight. This represents a conversion of 99%. At the beginning of the operative period the throughput was 8 liters/hour. In the course of the test the throughput decreased to 3 liters/hour. The test was terminated after an operating time of 1550 hours. A total of 5200 kg of glucose was converted; the sorbitol yield was 5205 kg.

Therefore, the quantity of sorbitol formed per quantity unit of catalyst—i.e., the mean catalyst activity ($\bar{a}_k$)—was 1668, which is 3.4 times as large as that obtained with the suspension hydrogenation in the Comparison Example. Accordingly, the catalyst requirement for the production of sorbitol by this process according to the invention was 0.06 percent by weight or, based upon the ruthenium, $1.2 \times 10^{-3}$ percent by weight.

The throughput of 50 percent by weight glucose solution determined over the total run was in the case of the solid bed hydrogenation according to the invention 5.5 liters/hour, i.e., 37.5 percent higher than with the suspension hydrogenation according to the prior art process of the Comparative Example.

EXAMPLE 2

The procedure described in Example 1 was modified in such a way that the throughput of 50 percent by weight glucose solution was maintained constant at 4 liters/hour. In the course of the run, the reaction temperature was raised from an initial temperature of 100° C. in steps of 10° C. in such a way that at least a conversion of 99% was obtained. The end temperature was 160° C. During the entire run a hydrogen pressure of 100 bar was maintained. At a charge of 2.96 kg of catalyst, a total of 8820 liters of glucose solution (5380 kg of glucose) was put through. The sorbitol yield was 5386 kg. Hence, the quantity of ruthenium required for the production of sorbitol from glucose was $1.1 \times 10^{-3}$ percent by weight, based upon the weight of the sorbitol obtained.

EXAMPLE 3

In analogy to Example 1, invert sugar in a 50 percent by weight solution was catalytically hydrogenated at 100° C. under a hydrogen pressure of 250 bar. The results regarding throughput and polyol yield were comparable to those for the glycose hydrogenation.

EXAMPLE 4

In analogy to Example 1, a corn starch hydrolyzate (DE=92) in a 40 percent by weight solution was catalytically hydrogenated at 150° C. under a hydrogen pressure of 250 bar. At an average throughput of 5 liters/hour a degree of conversion of 98%, based upon the content of reducing sugars, was obtained. The ruthenium requirement in the hydrogenation of the corn starch hydrolyzate was $1.3 \times 10^{-3}$ percent by weight, based upon polyols obtained.

From the results of the testing described above, it can be seen that the catalyst requirement is substantially smaller in the process according to the invention (Examples 1 to 4) than the known, continuous suspension hydrogenation process (the Comparison Example). This result was not predictable inasmuch as the catalysts used in the suspension process should, because of their small particle size, show a higher degree of pore utilization and hence a greater reactivity than the substantially coarser solid bed catalysts with particle diameters of from 2 to 10 mm, since it is known that the degree of pore utilization normally increases with decreasing catalyst particle diameter. Furthermore, one should expect for the suspension process a narrower residence time spectrum as compared to that of the solid bed process. It was therefore quite surprising to find that the solid bed process of the invention gave much more favorable values for the catalyst activity and for the means space-time yield in comparison to the suspension process.

The preceding specific embodiments are illustrative of the practice of the invention. It is to understood, however, that other expedients known to those skilled in the art or disclosed herein, may be employed without departing from the spirit of the invention or the scope of the appended claims.

We claim:

1. In a continuous process for preparing polyhydric alcohols by the hydrogenation of carbohydrates in the presence of ruthenium-containing catalysts at elevated temperature and elevated pressure, the improvement wherein the carbohydrates are in aqueous solution or in a colloidal solution or suspension in water and wherein the catalyst comprises a catalyst solid bed of ruthenium carrier catalyst in lumps.

2. The process of claim 1, wherein the lumps comprise catalyst particles in spherical, cylindrical, or hollow-cylindrical form.

3. The process of claim 2, wherein the catalyst particles have a particle size of from about 2 to 10 mm.

4. The process of claim 1, wherein the catalyst comprises from about 0.1 to 10 percent by weight, based upon the total weight of the catalyst, of ruthenium.

5. The process of claim 4, wherein the catalyst comprises from about 1 to 4 percent by weight, based upon the total weight of the catalyst, of ruthenium.

6. The process of claim 1, wherein the temperature is from about 60° to 200° C.

7. The process of claim 1, wherein the pressure is from about 25 to 300 bar.

8. The process of claim 1, wherein the carbohydrates are monosaccharides and the monosaccharides are in an aqueous solution having a pH of about 7.

9. The process of claim 1, wherein the carbohydrates partly or wholly comprise polysaccharides and the carbohydrates are in an aqueous solution having a pH of from about 2.5 to 4.5.

10. The process of claim 1, wherein the carbohydrates are in an aqueous solution comprising from about 20 to 80 percent by weight of carbohydrates.

11. The process of claim 10, wherein the aqueous solution comprises from about 40 to 70 percent by weight of carbohydrates.

* * * * *